(12) United States Patent
Gregg

(10) Patent No.: US 10,716,537 B2
(45) Date of Patent: Jul. 21, 2020

(54) ESOPHAGEAL ELECTROCARDIOGRAM FOR TRANSESOPHAGEAL ECHOCARDIOGRAPHY

(71) Applicant: KONINKLIJKE PHILIPS N.V., Eindhoven (NL)

(72) Inventor: Richard E. Gregg, Westford, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 612 days.

(21) Appl. No.: 15/501,093

(22) PCT Filed: Jul. 30, 2015

(86) PCT No.: PCT/IB2015/055747
§ 371 (c)(1),
(2) Date: Feb. 1, 2017

(87) PCT Pub. No.: WO2016/020800
PCT Pub. Date: Feb. 11, 2016

(65) Prior Publication Data
US 2017/0215840 A1 Aug. 3, 2017

Related U.S. Application Data

(60) Provisional application No. 62/034,194, filed on Aug. 7, 2014.

(51) Int. Cl.
*A61B 8/12* (2006.01)
*A61B 5/00* (2006.01)
(Continued)

(52) U.S. Cl.
CPC ............. *A61B 8/12* (2013.01); *A61B 5/0421* (2013.01); *A61B 5/7285* (2013.01); *A61B 8/00* (2013.01); *A61B 8/0883* (2013.01); *A61B 8/543* (2013.01)

(58) Field of Classification Search
CPC ....... A61B 8/12; A61B 5/0421; A61B 5/7285; A61B 8/00; A61B 8/0883; A61B 8/543
See application file for complete search history.

(56) References Cited

U.S. PATENT DOCUMENTS

| 4,817,611 A | 4/1989 | Arzbaecher et al. |
| 5,010,888 A | 4/1991 | Jadvar et al. |

(Continued)

FOREIGN PATENT DOCUMENTS

| DE | 2305501 A1 | 8/1974 |
| EP | 1749475 A2 | 2/2007 |

(Continued)

OTHER PUBLICATIONS

Flachskampf et al "Transoesophageal Stress Echocardiography" European Heart Journal (1997) 18, p. 37-42.

(Continued)

*Primary Examiner* — Lindsey G Wehrheim

(57) ABSTRACT

A medical imaging system employs a transesophageal probe (20) including an ultrasound transducer (21) for scanning a patient's heart and atrial electrode(s) (22) for generating atrial electrocardiogram signal(s) predominately indicative of electrical activity of atrium chambers of the patient's heart. The medical imaging system further employs ventricular electrode(s) (23) for generating ventricular electrocardiogram signal(s) predominately indicative of electrical activity of ventricle chambers of the patient's heart. The medical imaging system further employs an electrocardiogram machine (30) for generating an electrocardiogram waveform based on the indicated electrical activities of the patient's heart, and for generating a cardiac gating signal representative of a cyclical cardiac phase period of the electrocardiogram waveform. The medical imaging system further employs an ultrasound machine (40) for reconstruct- (Continued)

ing an ultrasound image of the patient's heart encompassing a time segment or an entirety of the cyclical cardiac phase period.

19 Claims, 4 Drawing Sheets

(51) Int. Cl.
*A61B 8/08* (2006.01)
*A61B 8/00* (2006.01)
*A61B 5/042* (2006.01)

(56) References Cited

U.S. PATENT DOCUMENTS

| | | | |
|---|---|---|---|
| 5,343,860 | A | 9/1994 | Metzger et al. |
| 5,749,833 | A | 5/1998 | Hakki et al. |
| 5,904,651 | A | 5/1999 | Swanson et al. |
| 5,967,977 | A | 10/1999 | Mullis et al. |
| 6,438,400 | B1 | 8/2002 | Beard et al. |
| 7,349,732 | B1 | 3/2008 | Kil et al. |
| 2004/0220471 | A1* | 11/2004 | Schwartz ............ A61B 5/0422 600/424 |
| 2007/0167801 | A1* | 7/2007 | Webler .................. G06T 19/00 600/459 |

FOREIGN PATENT DOCUMENTS

| | | |
|---|---|---|
| JP | 04176447 A | 6/1992 |
| WO | 2011097312 A1 | 8/2011 |
| WO | 2012160066 A1 | 11/2012 |

OTHER PUBLICATIONS

Falk et al "Transoesophageal Atrial Pacing Using a Pill Electrode for the Termination of Atrial Flutter" Chest, vol. 92, Issue 1 Jul. 1987 p. 110-114.

Roth et al "Positioning the Pacer Esophageal Stethoscope for Transesophageal Atrial Pacing Without P-Wave Recording . . . " Anesth. Analg. 1996, 83, p. 48-54.

* cited by examiner

ESOPHAGEAL ELECTROCARDIOGRAM FOR TRANSESOPHAGEAL ECHOCARDIOGRAPHY

This application is the U.S. National Phase application under 35 U.S.C. § 371 of International Application No. PCT/IB2015/055747, filed on Jul. 30, 2015, which claims the benefit of U.S. Provisional Application Ser. No. 62/034,194, filed Aug. 7, 2014. These applications are hereby incorporated by reference herein.

The present invention generally relates to transesophageal echocardiography ("TEE"). The present invention specifically relates to esophageal electrocardiogram ("ECG") for purposes of improving upon ultrasound scanning and image reconstruction aspects of TEE procedures.

TEE as known in the art is a procedure for generating high resolution images of a heart by use of high-frequency sound waves (i.e., ultrasound). For example, in a sagittal planar view 10 of a heart H and esophagus E as shown in FIG. 1, a TEE probe 20 having an ultrasound transducer 21 is passed through a patient's open mouth, down into the patient's throat and into the patient's esophagus E. Due to the proximity of esophagus E to a left atrium chamber LA, a right atrium chamber RA, a left ventricle chamber LV and a right ventricle chamber RV of heart H, very clear ultrasound images of the heart chambers and valves may be generated by an ultrasound machine 40 as known in the art. Please note, while in reality esophagus E is positioned behind and between a left atrium chamber LA and a right atrium chamber RA of heart H, FIG. 1 shows esophagus E is spaced from atrium chambers LA and RA for clarity of TEE probe 20.

ECG as known in the art is a procedure for recording electrical activity of chambers of a patient's heart by the strategic placements of electrodes relative to the patient's heart. For a standard non-invasive ECG, surface electrodes are strategically placed according to well established anatomical landmarks on a skin surface of the thoracic region of the patient as known in the art. However, disadvantages of surface electrodes include (1) a poor signal to noise ratio of an atrial component of surface ECG, (2) a masking of atrial component of ECG by the much larger ventricular component, and (3) a changing phase of atrial ECG activation compared to ventricular activation whereby traditional ECG gating impedes high resolution cine loops for the atrium chambers.

For a standard echocardiogram whereby a probe is placed on the skin surface of the thoracic region of the patient, an invasive ECG may be implemented in the form of a "pill" Electrode passed through a patient's open mouth, down into the patient's throat and into the patient's esophagus. The pill Electrode is utilized to diagnose difficult atrial arrhythmia, because the atrial signal is so strong and clear when it is measured near the atrium chambers from the esophagus. However, this procedure is not commonly used because of the inconvenience and uncomfortable nature of swallowing a pill on a string and pulling it back out. Moreover, the application of the pill Electrode has been restricted to ECG recording and pacing.

The present invention recognizes TEE probes are already near the heart with tight physical coupling to the esophagus for high resolution echocardiograms and a strong atrial ECG signal from the TEE probe would facilitate various novel applications for ultrasound imaging. For example, atrial ECG signal alone facilitates an automated detection and alarming for various form of atrial arrhythmia (e.g., atrial fibrillation, atrial flutter and atrial tachycardia). By further example, again using the strong atrial ECG signal, atrial gating of ultrasound is possible allowing for cine loops of the fast moving atrium chambers during high atrial rate arrhythmia.

One form of the present invention is a medical imaging system employing (1) a TEE probe including an ultrasound transducer and one or more atrial electrodes, (2) one or more ventricular electrodes, (3) an ECG machine, and (4) an ultrasound machine. In operation, the TEE probe is positioned in an esophagus of the patient adjacent a heart of the patient whereby the ultrasound transducer scans the patient's heart and whereby each atrial electrode on the TEE probe generates an atrial electrocardiogram signal predominately representative of electrical activity by atrium chambers of the patient's heart.

The ventricular electrode(s) are attached to a surface thoracic region of a patient whereby each ventricular electrode generates a ventricular signal predominately representative of electrical activity by ventricle chambers of the patient's heart.

The ECG machine generates an electrocardiogram waveform of the patient's heart from the indicated electrical activities of the chambers of the patient's heart, and additionally generates a cardiac gating signal indicative of a cyclical cardiac phase period of the electrocardiogram waveform.

From the ultrasound scanning of the patient's heart and a generation of the cardiac gating signal, the ultrasound machine reconstructs an ultrasound image of the patient's heart encompassing a time-segment or an entirety of the cyclical cardiac phase period of the electrocardiogram waveform.

For example, the ECG machine may derive the cardiac gating signal from a normal atrial phase of the electrocardiogram waveform (e.g., a P-wave trigger) or a normal ventricular phase of the electrocardiogram waveform (e.g., a QRS complex trigger) whereby the cardiac gating signal triggers a control by the ultrasound machine of the ultrasound scanning of the patient's heart by the ultrasound transducer and/or an image reconstruction of the patient's heart during a time segment or an entirety of the cyclical cardiac phase period of the electrocardiogram waveform.

Concurrently or alternatively, the ECG machine may derive the cardiac gating signal from a detection by the ECG machine of an atrial phase of an atrial arrhythmia of the electrocardiogram waveform (e.g., atrial ECG gating for atrial fibrillation, atrial flutter and atrial tachycardia) whereby the cardiac gating signal again triggers a control by the ultrasound machine of the ultrasound scanning of the patient's heart by the ultrasound transducer and/or an image reconstruction of the patient's heart during a time segment or an entirety of the cyclical cardiac phase period of the electrocardiogram waveform. Note this atrial ECG gating is useful for atrial imaging for any arrhythmia where (a) the atrial and ventricular activities overlap, (b) the atrial and ventricular rates are different or (c) a phase between atrial and ventricular activities varies. In particular, for some atrial arrhythmia's like atrial flutter, there are multiple atrial cycles for each ventricular cycle and the atrial and ventricular activity are completely overlapped in time. Often, the number of atrial cycles per ventricular cycle varies.

The foregoing form and other forms of the present invention as well as various features and advantages of the present invention will become further apparent from the following detailed description of various embodiments of the present invention read in conjunction with the accompanying drawings. The detailed description and drawings are merely illustrative of the present invention rather than limiting, the scope of the present invention being defined by the appended claims and equivalents thereof.

For purposes of the present invention, the structural terms "transesophageal probe", "ultrasound transducer", "electrode", "ECG machine" and "ultrasound machine" as well as synonymous and related terms are to be broadly interpreted as known in the art of the present invention.

Figure 1:
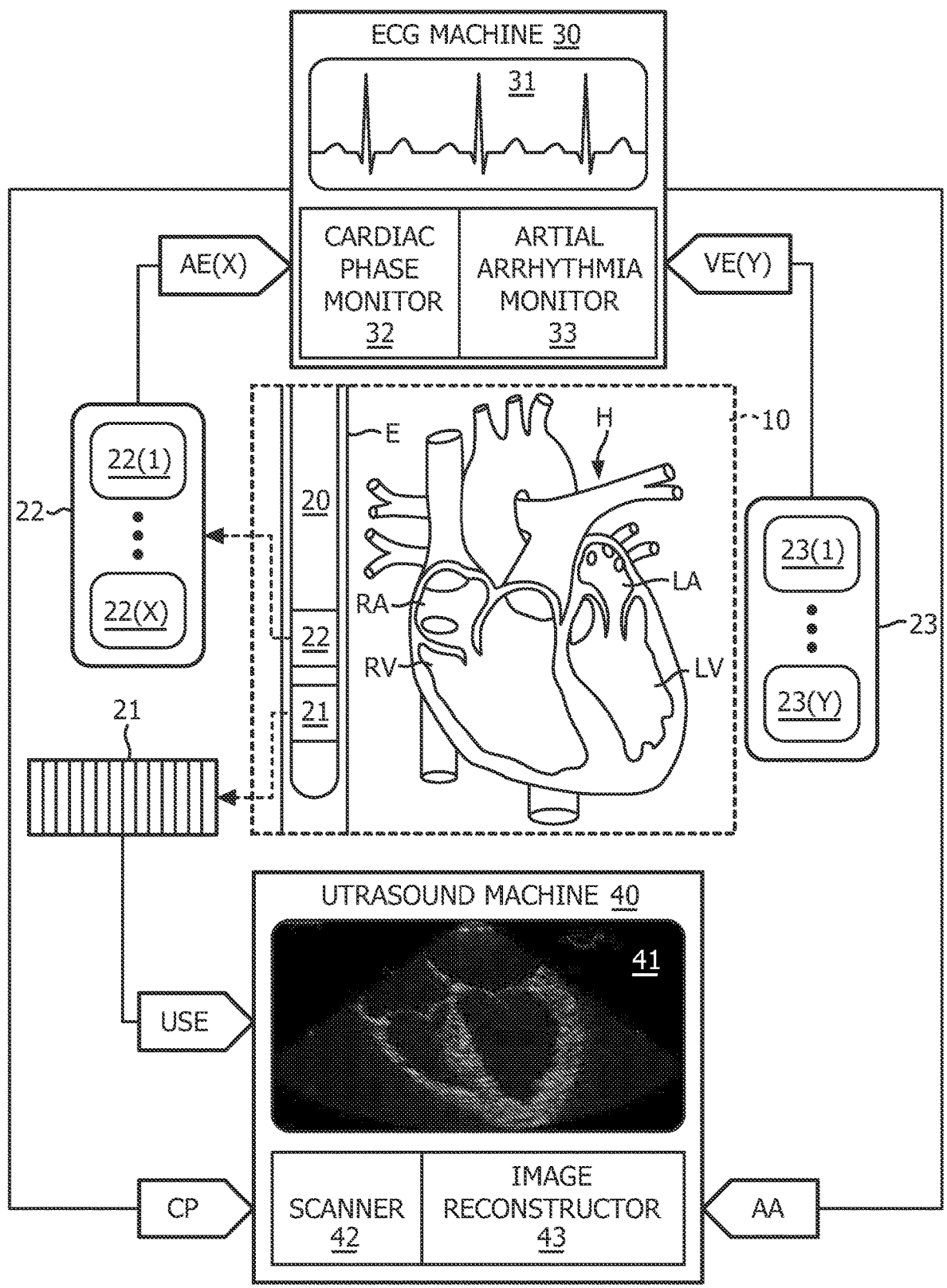
FIG. 1 illustrates an exemplary embodiment of a medical imaging system in accordance with the present invention.

To facilitate an understanding of the present invention, exemplary embodiments of the present invention will be provided herein directed to an esophageal ECG for purposes of improving upon ultrasound scanning and image reconstruction aspects of a TEE procedure as implemented by a medical imaging system of the present invention as shown in FIG. 1 employing (1) TEE probe 20 having ultrasound transducer 21 and an X number of atrial electrodes 22, X≥1, (2) a Y number of ventricular electrodes 23, Y≥1, (3) an ECG machine 30 and (4) ultrasound machine 40.

Referring to FIG. 1, as previously stated herein, the TEE procedure involves TEE probe 20 being passed through a patient's open mouth, down into the patient's throat and into the patient's esophagus E. Due to the proximity of esophagus E to heart H, the chambers and valves of heart H may be clearly scanned by ultrasound transducer 21 as known in the art. In accordance with the present invention, the TEE procedure involves a novel arrangement atrial electrodes 22 on TEE probe 20 whereby electrical activity of atrium chambers RA and LA may be directly sensed by atrial electrode(s) 22 also due to the proximity of esophagus E to heart H.

The TEE procedure further involves an arrangement of ventricular electrodes 23 on a surface thoracic region of the patient as known in the art whereby electrical activity of ventricle chambers RV and LV may be directly sensed by ventricular electrode(s) 23 as known in the art.

Each atrial ECG electrode 22 generates and communicates an atrial ECG signal AE to an ECG machine 30, and each ventricular electrode 23 generates and communicates a ventricular ECG signal VE to ECG machine 30 whereby ECG machine 30 generates an ECG waveform as known in the art, such as, for example, a normal ECG waveform 31 as shown. Each atrial ECG signal AE is predominately indicative of electrical activity by atrium chambers RA and LA of the heart H, and each ventricular ECG signal VE is predominately indicative of electrical activity by ventricle chambers RV and LV of the heart H. Consequently, a normal ECG waveform generated by ECG machine 30 (e.g., ECG waveform 31 as shown) is optimal in view of an atrial phase of the ECG waveform (i.e., atrial depolarization and atrioventricular node delay) being derived from a direct sensing of atrium chambers RA and LA, and in view of a ventricular phase of the ECG waveform (i.e., atrial depolarization and/or ventricular repolarization) being derived from a direct sensing of ventricle chambers RV and LV. Additionally, a presence of an atrial phase of an arrhythmia of an abnormal ECG waveform (not shown in FIG. 1) is more easily detected via each atrial ECG signal AE similar to the way pacemakers use different connections to pick up signals emphasizing atrial electrical activity rather than ventricular electrical activity.

For cardiac gating purposes based on the advantages of ECG signals AE and VE of the present invention, ECG machine 30 incorporates a cardiac phase monitor 32 and an atrial arrhythmia monitor 33 as hardware, software, firmware and/or circuit modules in a segregated form or integrated into an existing module (e.g., an automated ECG analyzing unit as known in the art).

Cardiac phase monitor 32 monitors one or both ECG signals AE and VE to detect each atrial phase of a normal ECG waveform or each ventricular phase of a normal ECG waveform. From each detection of a designated cardiac phase (i.e., atrial or ventricular), cardiac phase monitor 32 generates and communicates a cardiac gating signal in the form of a cardiac phase signal CP to ultrasound machine 40.

For atrial phase detection, cardiac phase monitor 32 processes both ECG signals AE and VE or exclusively processes atrial ECG signal(s) AE in detecting each atrial phase of a normal ECG waveform, and communicates cardiac phase signal CP as a scanning and/or image reconstruction trigger for ultrasound machine 40 (e.g., a P-wave trigger).

For ventricular phase detection, cardiac phase monitor 32 processes both ECG signals AE and VE or exclusively processes ventricular ECG signal(s) VE in detecting each ventricular phase of a normal ECG waveform, and communicates cardiac phase signal CP as a scanning and/or image reconstruction trigger for ultrasound machine 40 (e.g., a QRS complex trigger).

Atrial arrhythmia monitor 33 monitors one or both ECG signals AE and VE to detect any presence of an atrial arrhythmia phase of an abnormal ECG waveform (e.g., atrial fibrillation, atrial flutter and atrial tachycardia), and communicates a cardiac gating signal in the form of an arrhythmia alarm signal AA to ultrasound machine 40. Preferably, atrial arrhythmia monitor 33 exclusively monitor atrial ECG signal(s) AE in detecting any presence of an atrial arrhythmia phase of an abnormal ECG waveform.

Ultrasound machines 40 incorporates a scanner 42 as known in the art for controlling a scanning of heart H by ultrasound transducer 21, and an image reconstructor 43 as known in the art for image reconstructing an ultrasound image of heart H from ultrasound echo signals USE received from ultrasound transducer 21. In practice, ultrasound transducer 21 may be any type of ultrasound transducer as known in the art (e.g., two-dimensional or three-dimensional, linear or curved, etc.) and scanner 42 and image reconstructor 43 are structurally configured in accordance with the type of ultrasound transducer.

For purposes of the present invention, scanner 42 and/or image reconstructor 43 are further structurally configured to execute respective scanning and image reconstruction tasks as triggered by cardiac phase signal CP and/or as triggered by arrhythmia alarm signal AA.

Figure 2:
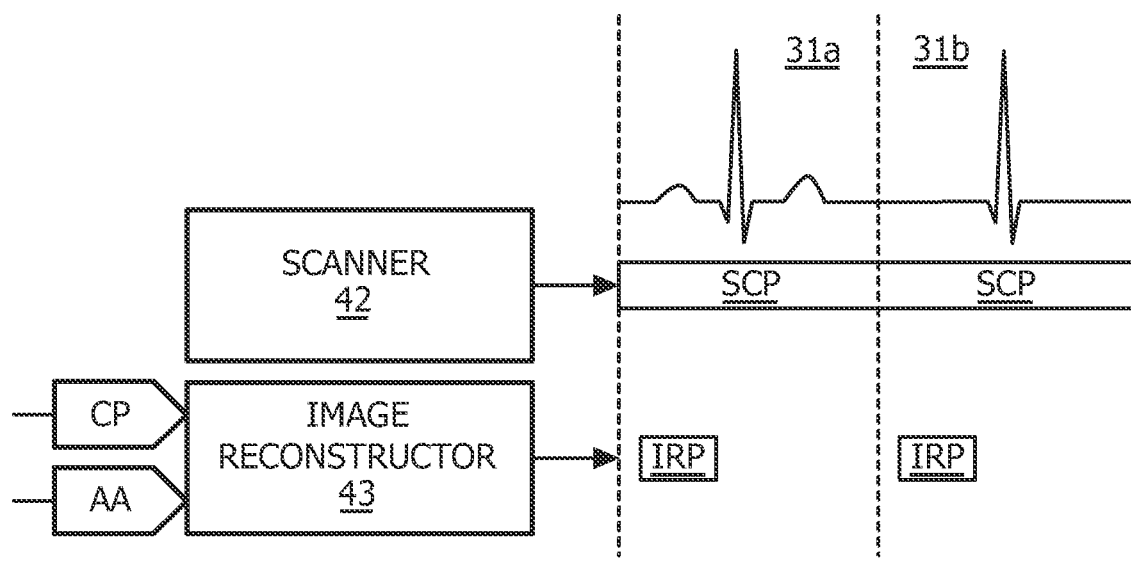
FIGS. 2-4 illustrate exemplary cardiac gating in accordance with the present invention.

For example, as shown in FIG. 2, scanner 42 is structurally configured to execute the scanning task over a continuous scanning period SCP, and image reconstructor 43 is structurally configured to execute the image reconstruction task during a cyclical image reconstruction period IRP as triggered by cardiac phase signal CP for atrial phase detection or as triggered by arrhythmia alarm signal AA. For a normal ECG waveform 31a, image reconstruction period IRP encompasses a portion (e.g., P-wave only) or an entirety of the atrial phase as triggered by cardiac phase signal CP. For an abnormal ECG waveform 31b, image reconstruction period IRP preferably encompasses an entirety of the atrial phase as triggered by arrhythmia alarm signal AA. To this end, image reconstructor 43 may be structurally configured whereby arrhthymia alarm signal AA overrides cardiac phase signal CP whenever an atrial arrhythmia is detected by monitor 33 (FIG. 1).

Figure 3:
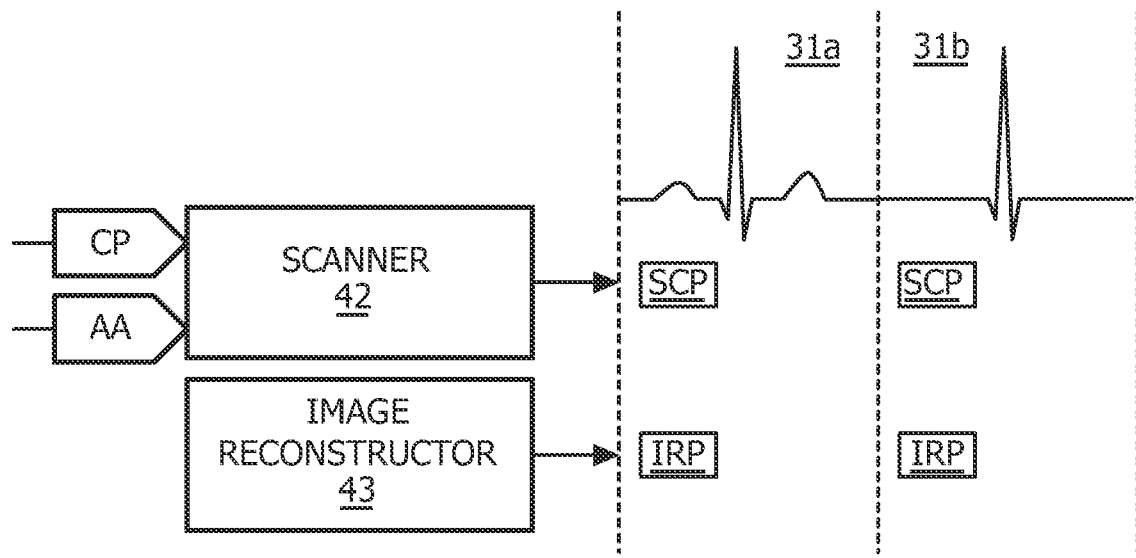

Also by example, as shown in FIG. 3, scanner 42 is structurally configured to execute the scanning task during a cyclical scanning period SCP as triggered by cardiac phase signal CP for atrial phase detection or as triggered by arrhythmia alarm signal AA, and image reconstructor 43 is structurally configured to execute the image reconstruction task during cyclical image reconstruction period IRP coinciding with scanning period SP. For a normal ECG waveform 31a, scanning period SCP and image reconstruction period IRP encompass a portion (e.g., P-wave only) or an entirety of the atrial phase as triggered by cardiac phase signal CP. For an abnormal ECG waveform 31b, image scanning period SCP and reconstruction period IRP preferably encompass an entirety of the atrial phase as triggered by arrhythmia alarm signal AA. To this end, scanner 42 may be structurally configured whereby arrhthymia alarm signal AA overrides cardiac phase signal CP whenever an atrial arrhythmia is detected by monitor 33 (FIG. 1).

Figure 4A:
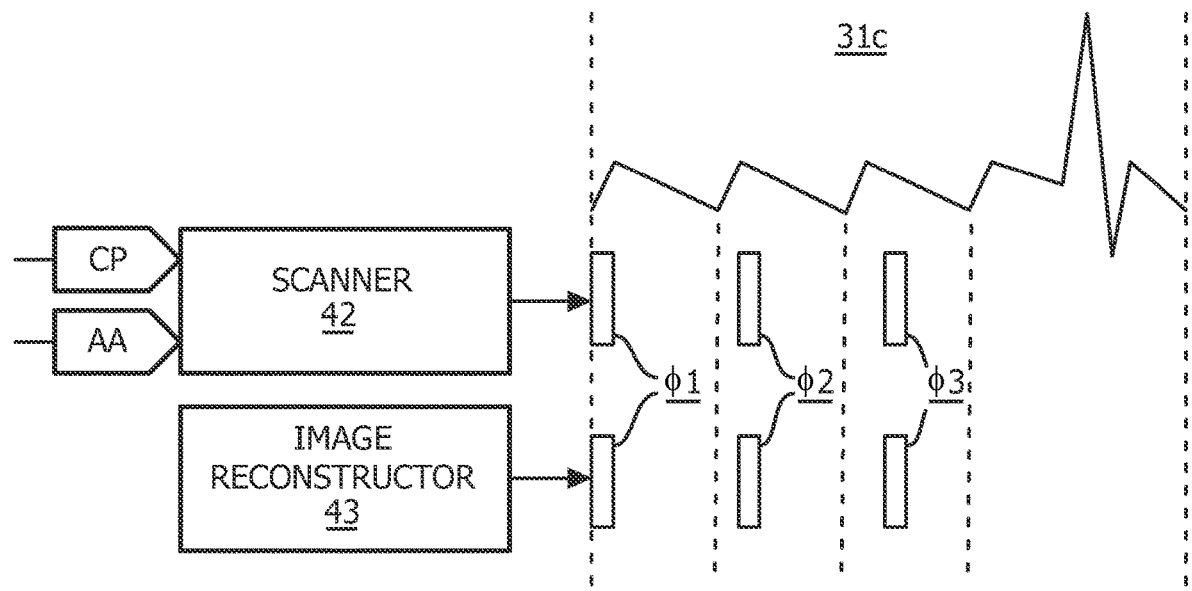
Figure 4B:
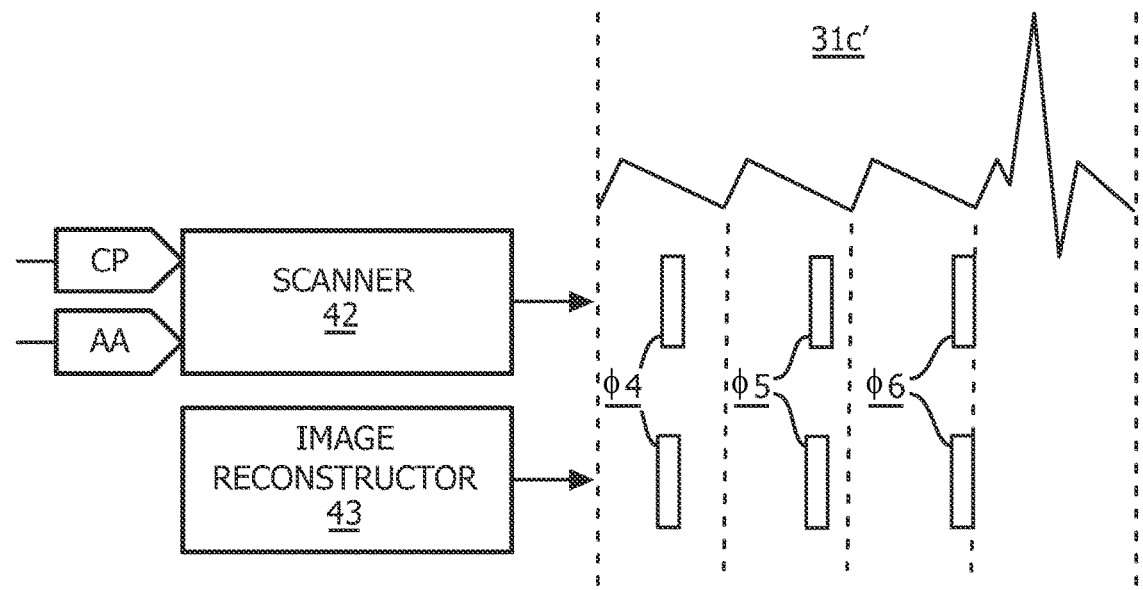

By further example, as exemplary shown in FIG. 4, an atrial flutter waveform 31c involves multiple atrial cycles (i.e., F-waves) prior to the QRS complex for each ventricular cycle (i.e., T-wave). For this waveform 31c, the atrial electrical activity and the ventricular electrical activity are overlapped in time whereby a number of atrial cycles per ventricular cycle may vary and whereby a phase between an atrial cycle and the QRS complex may vary as shown between FIGS. 4A and 4B. To this end, scanner 42 is structurally configured to execute the scanning task in phases φ as triggered by arrhythmia alarm signal AA, and image reconstructor 43 is structurally configured to execute the image reconstruction task coinciding with scanning phases φ. More particularly, as exemplary shown in FIG. 4, six (6) phases φ are varied slices of each atrial cycle in an effort to build a single longer period image over multiple atrial cycles to show a single complete atrial cycle as would be appreciated by those having ordinary skill in the art (e.g., similar to building a larger 3D ultrasound image from smaller subvolumes captured across many heart beats).

From the description of FIGS. 2-4, those having ordinary skill in the art will appreciate in practice that scanner 42 and/or image reconstructor 43 may be triggered by cardiac phase signal CP and/or triggered by arrhythmia alarm signal AA to execute respective scanning and image reconstruction tasks in various and numerous operational modes.

Figure 5:
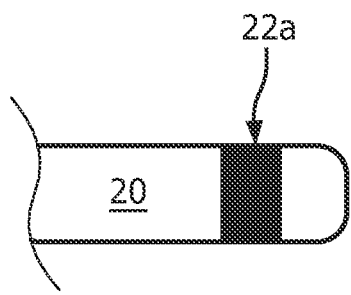
FIGS. 5-7 illustrate exemplary embodiments of atrial electrodes in accordance with present invention.
Figure 6:
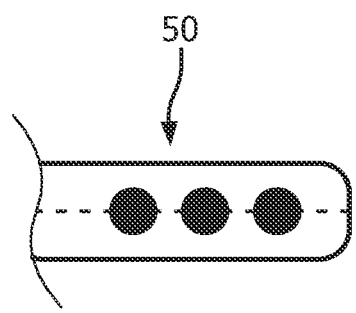
Figure 7:
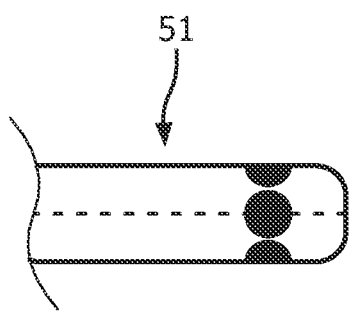

Referring back to FIG. 1, in practice, each atrial electrode 22 may have structural form suitable for directly sensing electrical activity of atrium chambers of heart H. For example, each atrial electrode 22 may have a lead form as known in the art, or be an electrode ring 22a disposed around TEE probe 20 as shown in FIG. 5. Also in practice, multiple atrial electrode 22 may be arranged on TEE probe 22 in a manner suitable for directly sensing electrical activity of atrium chambers of heart H. For example, atrial electrodes 22 may have a linear arrangement 50 parallel to a longitudinal axis of TEE probe 20 indicated by the dashed line as shown in FIG. 6 or may have a circular arrangement 51 perpendicular to the longitudinal axis of TEE probe 20 as shown in FIG. 7.

Also in practice, a pair of atrial electrodes 22 or a pairing of an atrial electrode 22 and a ventricular electrode 23 may be utilized to generate a bipolar ECG signal. Such pairings will enhance the cardiac gating feature of ECG machine 30. More particularly, a bipolar difference between electrodes enhances the signal amplitude along the physical axis of the bipolar electrode pair so that different bipolar combinations can be used to enhance signal amplitude in various parts of the heart whereby the electrical conduction goes in the direction of the bipolar electrode pair. This is the reason for multiple ECG electrodes for diagnostic ECG.

Referring to FIGS. 1-7, those having ordinary skill in the art will appreciate numerous benefits of the present invention including, but not limited to, an atrial arrhythmia alarm during a TEE procedure that may be used for cardiac gating purposes to display cine loops of fast moving atrial phases. For example, referring to FIG. 4, through short scan periods at varied phases of an atrial depolarization across multiple atrial cycles, a very high resolution image may be generated of the atrial depolarization.

While various embodiments of the present invention have been illustrated and described, it will be understood by those skilled in the art that the embodiments of the present invention as described herein are illustrative, and various changes and modifications may be made and equivalents may be substituted for elements thereof without departing from the true scope of the present invention. In addition, many modifications may be made to adapt the teachings of the present invention without departing from its central scope. Therefore, it is intended that the present invention not be limited to the particular embodiments disclosed as the best mode contemplated for carrying out the present invention, but that the present invention includes all embodiments falling within the scope of the appended claims.

The invention claimed is:

1. A medical imaging system for ultrasound imaging a heart of a patient, the medical imaging system comprising:
    a transesophageal probe operable to be positioned in an esophagus of the patient adjacent the heart,
        wherein the transesophageal probe includes an ultrasound transducer operable to scan the heart, and
        wherein the transesophageal probe further includes at least one atrial electrode, each atrial electrode being operable to generate an atrial electrocardiogram signal predominately indicative of electrical activity by atrium chambers of the heart;
    at least one ventricular electrode operable to be attached to a surface thoracic region of the patient, each ventricular electrode is further operable to generate a ventricular electrocardiogram signal predominately indicative of electrical activity by ventricle chambers of the heart;
    an electrocardiogram machine operable to generate an electrocardiogram waveform of the heart responsive to a generation of the at least one atrial electrocardiogram signal by the at least one atrial electrode and responsive to a generation of the at least one ventricular electrocardiogram signal by the at least one ventricular electrode,
        wherein the electrocardiogram machine is further operable to generate a cardiac gating signal indicative of a cyclical cardiac phase period of the electrocardiogram waveform; and
    an ultrasound machine to reconstruct at least one ultrasound image of the heart encompassing at least a portion of the cyclical cardiac phase period of the electrocardiogram responsive to an ultrasound scanning of the heart by the ultrasound transducer and responsive to a generation of the cardiac gating signal by the electrocardiogram machine.

2. The medical imaging system of claim 1, wherein the electrocardiogram machine includes a cardiac phase monitor operable to derive the cyclical cardiac phase period from a normal atrial phase of the electrocardiogram waveform.

3. The medical imaging system of claim 1, wherein the electrocardiogram machine includes a cardiac phase monitor operable to derive the cyclical cardiac phase period from a normal ventricular phase of the electrocardiogram waveform.

4. The medical imaging system of claim 1, wherein the electrocardiogram machine includes an atrial arrhythmia monitor operable to derive the cyclical cardiac phase period from an atrial arrhythmia phase of the electrocardiogram waveform.

5. The medical imaging system of claim 1, wherein the electrocardiogram machine generates the electrocardiogram waveform as a function of a bipolar signal derived from a pair of atrial electrodes.

6. The medical imaging system of claim 1, wherein the electrocardiogram machine generates the electrocardiogram waveform as a function of a bipolar signal derived from an atrial electrode and a ventricular electrode.

7. The medical imaging system of claim 1, wherein the electrocardiogram machine generates the electrocardiogram waveform as a function of a signal derived from a combination of the at least one atrial electrode and the at least one ventricular electrode.

8. The medical imaging system of claim 1, wherein each atrial electrode is a ring electrode externally disposed around the transesophageal probe.

9. The medical imaging system of claim 1,
wherein the ultrasound machine includes a scanner operable to control the ultrasound scanning of the heart by the ultrasound transducer during a cyclical scanning period; and
wherein the scanner derives the cyclical scanning period from the cyclical cardiac phase period.

10. The medical imaging system of claim 1,
wherein the ultrasound machine includes an image reconstructor operable to image reconstruct the ultrasound image of the heart during a cyclical image reconstruction period; and
wherein the image reconstructor derives the cyclical image reconstruction period from the cyclical cardiac phase period.

11. The medical imaging system of claim 1,
wherein the ultrasound machine includes an image reconstructor operable to image reconstruct the ultrasound image of the heart during a cyclical image reconstruction period; and
wherein the image reconstructor derives the cyclical image reconstruction period as a larger three dimensional ultrasound cine loop made from smaller subvolumes.

12. An imaging system in communication with an electrocardiogram machine and an ultrasound probe configured to internally image a heart of a subject, the imaging system configured to:
receive, from the electrocardiogram machine, a cardiac phase signal corresponding to an
electrocardiogram waveform generated from both an atrial electrocardiogram signal and a ventricular electrocardiogram signal;
receive, from the ultrasound probe, ultrasound echo signals from the subject's heart over a plurality of cardiac cycles; and
use the cardiac phase signal to trigger image reconstruction of the heart from a portion of the ultrasound echo signals corresponding to a specific time segment of the plurality of cardiac cycles.

13. A transesophageal probe operable to be positioned in an esophagus of a patient adjacent the heart, the transesophageal probe, comprising:
an ultrasound transducer operable to scan the heart, and
at least one atrial electrode, each atrial electrode being operable to generate an atrial electrocardiogram signal predominately indicative of electrical activity by atrium chambers of the heart,
wherein an atrial electrocardiogram waveform is generated as a function of a bipolar signal derived, at least in part, from the at least one atrial electrode.

14. The transesophageal probe of claim 13, wherein each of the at least one atrial electrode is a ring electrode externally disposed around the transesophageal probe.

15. An electrocardiogram machine operably connectable to at least one atrial electrode disposed in a transesophageal probe;
wherein each atrial electrode is operable to generate an atrial electrocardiogram signal predominately indicative of electrical activity by atrium chambers of the heart; and
wherein the electrocardiogram machine is operable to generate an electrocardiogram waveform of the heart responsive to a generation of the at least one atrial electrocardiogram signal by the at least one atrial electrode,
wherein the electrocardiogram machine includes one of either a cardiac phase monitor operable to derive the cyclical cardiac phase period from a normal atrial phase of the electrocardiogram waveform or an atrial arrhythmia monitor operable to derive the cyclical cardiac phase period from an atrial arrhythmia phase of the electrocardiogram waveform.

16. The electrocardiogram machine of claim 15, wherein the electrocardiogram machine generates the electrocardiogram waveform as a function of a bipolar signal derived from a pair of atrial electrodes.

17. The electrocardiogram machine of claim 15, wherein the electrocardiogram machine is further operably connectable to at least one ventricular electrode operable to be attached to a surface thoracic region of a patient, and each ventricular electrode is further operable to generate a ventricular electrocardiogram signal predominately indicative of electrical activity by ventricle chambers of the heart.

18. The electrocardiogram machine of claim 17, wherein the electrocardiogram machine generates the electrocardiogram waveform as a function of a bipolar signal derived from an atrial electrode and a ventricular electrode.

19. The electrocardiogram machine of claim 17, wherein the electrocardiogram machine generates the electrocardiogram waveform as a function of a signal derived from a combination of the at least one atrial electrode and the at least one ventricular electrode.

* * * * *